United States Patent [19]
Wood

[11] Patent Number: 5,690,223
[45] Date of Patent: *Nov. 25, 1997

[54] STERILIZATION AND STORAGE CONTAINER

[75] Inventor: Timothy E. Wood, Weare, N.H.

[73] Assignee: Poly Vac Incorporated, Manchester, N.H.

[*] Notice: The term of this patent shall not extend beyond the expiration date of Pat. No. 5,595,296.

[21] Appl. No.: 677,641

[22] Filed: Jul. 9, 1996

Related U.S. Application Data

[63] Continuation of Ser. No. 388,287, Feb. 14, 1995, Pat. No. 5,595,296.

[51] Int. Cl.$^6$ .................................... B65D 51/16
[52] U.S. Cl. ..................... 206/363; 206/439; 206/562; 220/525; 422/300
[58] Field of Search ..................... 206/363–370, 206/379, 380, 382, 438, 439, 459.5, 562; 220/524, 525; 422/500, 310

[56] References Cited

U.S. PATENT DOCUMENTS

| | | | |
|---|---|---|---|
| 4,783,321 | 11/1988 | Spence | 206/439 |
| 4,798,292 | 1/1989 | Hauze | 206/439 |
| 5,307,933 | 5/1994 | Gruignet et al. | 206/562 |
| 5,324,489 | 6/1994 | Nichols et al. | 206/363 |
| 5,394,983 | 3/1995 | Latulippe et al. | 206/562 |
| 5,441,707 | 8/1995 | Lewis et al. | 206/439 |
| 5,524,755 | 6/1996 | Deeds | 206/439 |
| 5,573,741 | 11/1996 | Riley | 206/439 |

*Primary Examiner*—Paul T. Sewell
*Assistant Examiner*—Luan K. Bui
*Attorney, Agent, or Firm*—Hayes, Soloway, Hennessey, Grossman & Hage. P.C.

[57] ABSTRACT

A surgical container for sterilizing, transporting and storing small surgical instruments such as drill, pins, screws and the like. The container comprises a base having at least one well, and includes an apertured plate for holding the instruments, covering the well at least in part. The apertured plate has apertures sized to accommodate selected instruments, and a cover rotatably mounted over the apertured plate. The cover has an opening for providing access to a limited area of the plate and any instruments loaded therein.

15 Claims, 4 Drawing Sheets

STERILIZATION AND STORAGE CONTAINER

This is a continuation of Ser. No. 08/388,287, filed on Feb. 14, 1995, now U.S. Pat. No. 5,595,296.

FIELD OF THE INVENTION

This invention relates to sterile container systems generally, and more particularly to container systems for the sterilization and subsequent sterile storage of medical surgical instruments and the like.

Sterilization of precision surgical instruments and their subsequent sterile storage is of paramount concern to surgeons and hospitals. Sterilized surgical instruments are essential during surgical procedures to minimize the risk of infection.

Some example prior art patents which provide for sterilization and storage of surgical instruments are Arp et al, U.S. Pat. No. 4,643,303; Nichols, U.S. Pat. No. 4,728,504, and Spence, U.S. Pat. No. 4,783,321. These prior art patents generally teach the use of baskets or trays to hold the instruments to be sterilized, and include apertures in the baskets which allow for gross drainage of condensation from the baskets first to the container floor below the basket, and from the container floor to the outside.

U.S. Pat. No. 4,643,303 describes a sterilization container enclosing an instrument basket within a box-like base and cover. The container also includes clamps mounted to the container by hinges for releasably holding the cover to the base. U.S. Pat. No. 4,783,321 describes a sterilization container enclosing an instrument basket within base and cover. The container also includes a latch mechanism for releasably holding the cover to the base.

Hauze, U.S. Pat. No. 4,798,292, describes a non-locking sterilization container with apertures arranged in rows and columns enclosing a flat surfaced insert with apertures arranged in rows and columns such that the apertures in the container and the insert are vertically aligned. Pegs are inserted in the insert apertures to provide horizontal separation of the instruments during sterilization and subsequent presentation of the instruments.

Brooks, U.S. Pat. No. 5,098,676 describes an improved sterilization tray assembly for sterilizing, transporting and storing instruments, comprising an upper tray section including a plurality of upper tray ports spaced in a predetermined pattern; a lower tray section including a plurality of lower tray ports spaced in a predetermined pattern; and locking means for engaging the upper tray section and the lower tray section to form a sealing contact between the upper and lower tray sections. A mat made of silicone rubber and sized to fit the tray is positioned between the tray sections. The mat has an upper surface and a lower surface, and includes a plurality of ports in the mat spaced in a predetermined pattern wherein the mat ports and the lower tray ports are in vertical alignment. The mat also has a plurality of upwardly tapered, vertical projections spaced in a predetermined pattern on the upper surface, the vertical projections having tips at their free ends to provide support for instruments above the upper surface; and a plurality of downwardly projecting support feet depending from the lower surface spaced in a predetermined pattern for spacing the lower surface above the lower tray section.

The sterilization tray assembly as described in Brooks U.S. Pat. No. 5,098,676 is available commercially from PolyVac, Inc. of Manchester, N.H., and has achieved substantial commercial success. However, while the silicone rubber mat as described in U.S. Pat. No. 5,098,676 provides a convenient support for larger surgical instruments, smaller instruments such as drill bits, pins, screws and the like may not be securely held. Accordingly, PolyVac, Inc. and others have introduced sterilization trays including one or more holding strips specifically designed to releasably hold selected surgical instruments.

In copending application Ser. No. 08/355,997 filed Dec. 14, 1994, assigned to a common assignee, there is disclosed a sterilization, transporting and storage container tray assembly for a surgical instrument kit, which includes a rack assembly having a plurality of spaced apertures for accommodating small surgical instruments such as drills, pins, screws or the like. The apertures have i.d.'s selected for accommodating the selected instruments, etc. so that the instruments readily may be loaded into the rack for sterilization, and readily may be removed by the surgeon during an operation. The rack is rotatably mounted in the storage container bottom tray or in an instrument tray loaded in the bottom tray so that the rack may be rotated to a horizontal position to reduce the possibility that the instruments loaded therein might be dislodged during transport. The rack rotatable mounting also permits the user to orient the rack at an angle which facilitates both the identification and removal of the small instruments.

SUMMARY OF THE INVENTION

The present invention provides an improved sterilization, transporting and storage container for small instruments such as drills, pins, screws and the like, and which comprises an apertured base member having at least one hollow, and having an apertured plate covering the at least one hollow at least in part. The apertured plate has apertures sized to accommodate selected instruments. A cover rotatably mounted over the apertured plate has a slot for providing access to a limited area of the plate and the instruments loaded therein. In a preferred embodiment of the invention, the container includes one or more additional hollows or wells which are selectively covered by a slidably mounted cover. In another and preferred embodiment the invention includes means for releasably storing an extraction tool for facilitating removal of instruments loaded in the plate.

BRIEF DESCRIPTION OF THE DRAWINGS

The foregoing and other objects of the present invention and various features and details of the operation and construction thereof are hereinafter more fully set forth with reference to the accompanying drawings, wherein like numerals depict like parts, and wherein.

DETAILED DESCRIPTION OF A PREFERRED EMBODIMENT

Figure 1:
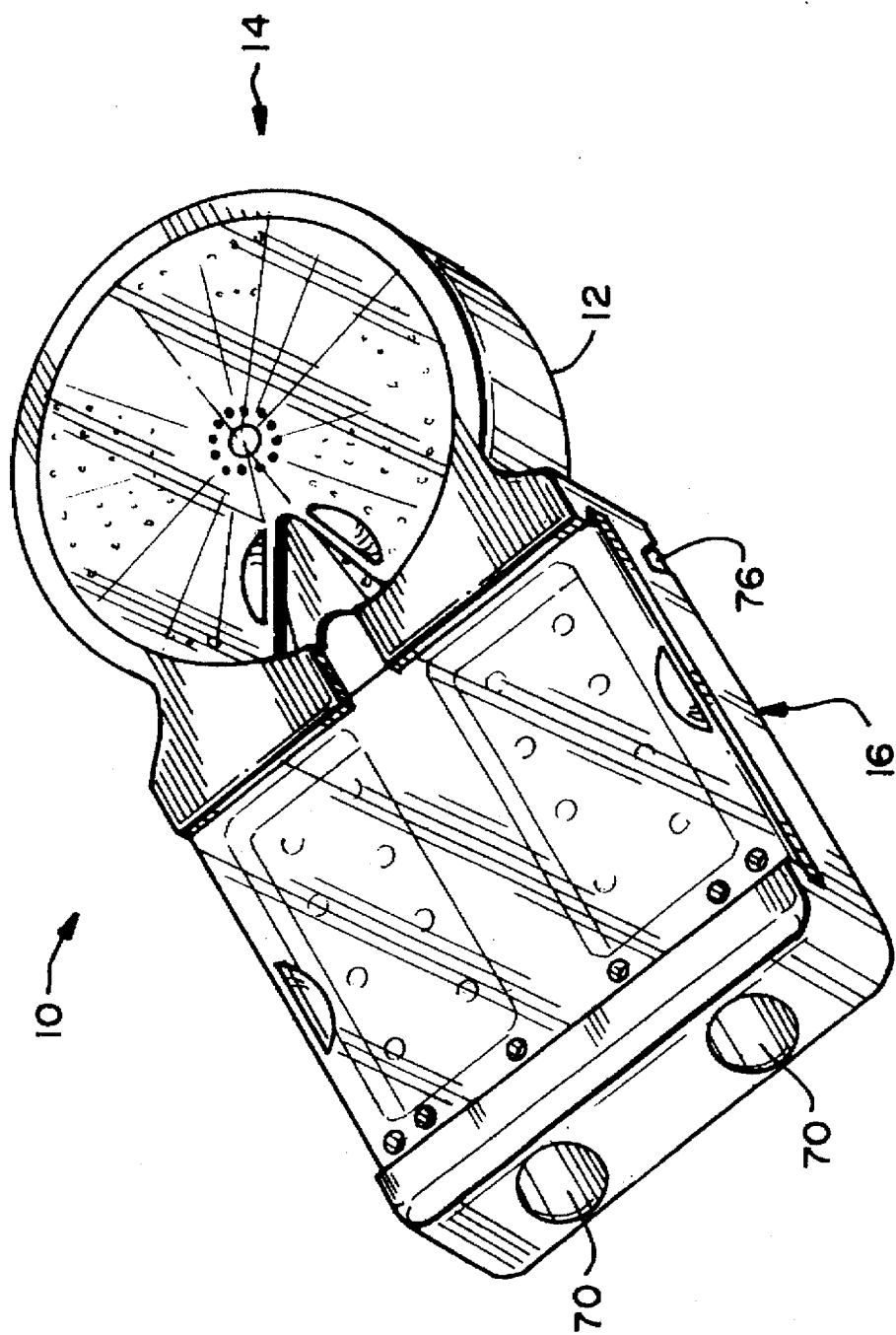
FIG. 1 is a perspective view of the preferred embodiment of the invention showing the sterilization and storage container in a closed position.
Figure 2:
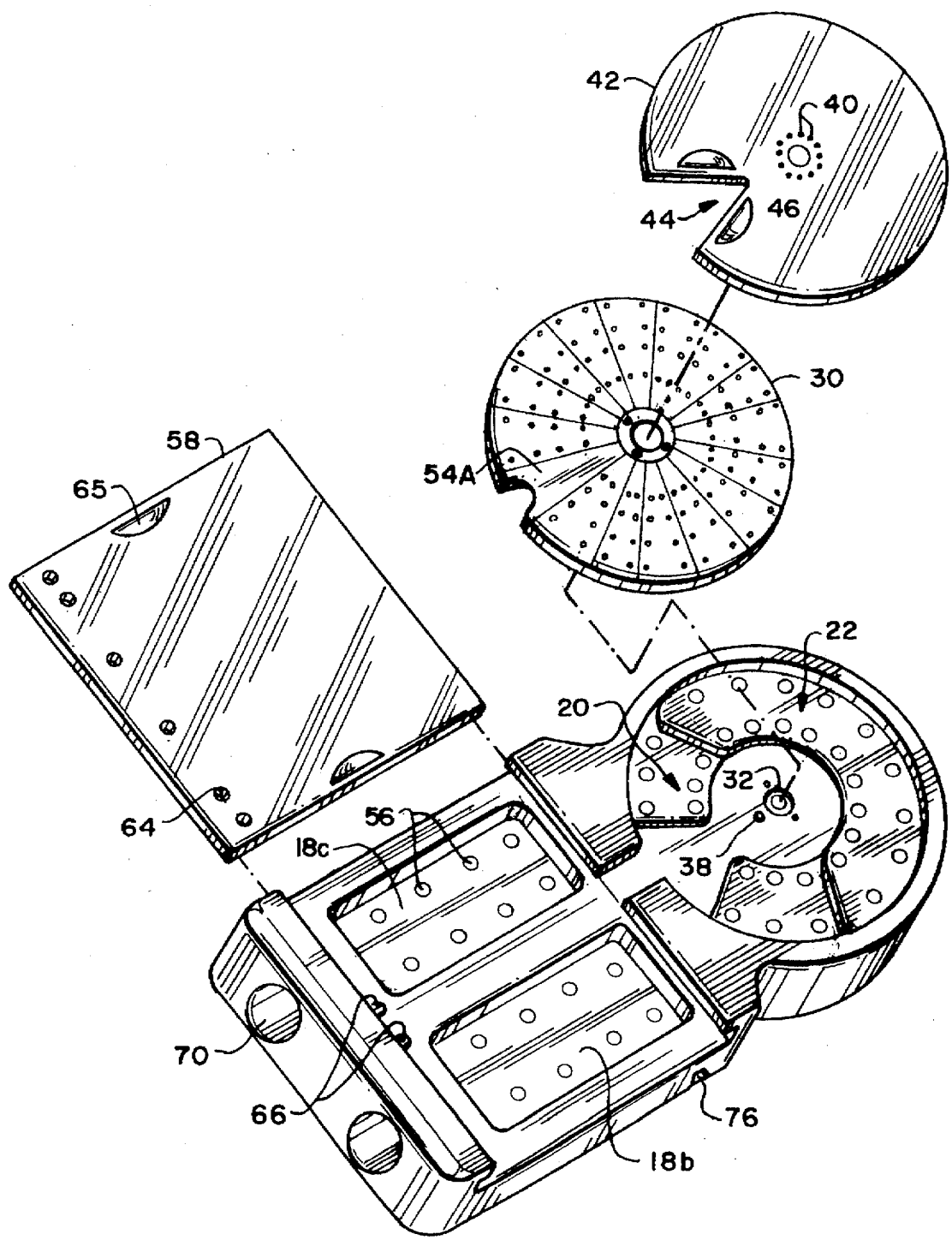
FIG. 2 is a partially exploded view of FIG. 1.
Figure 3:
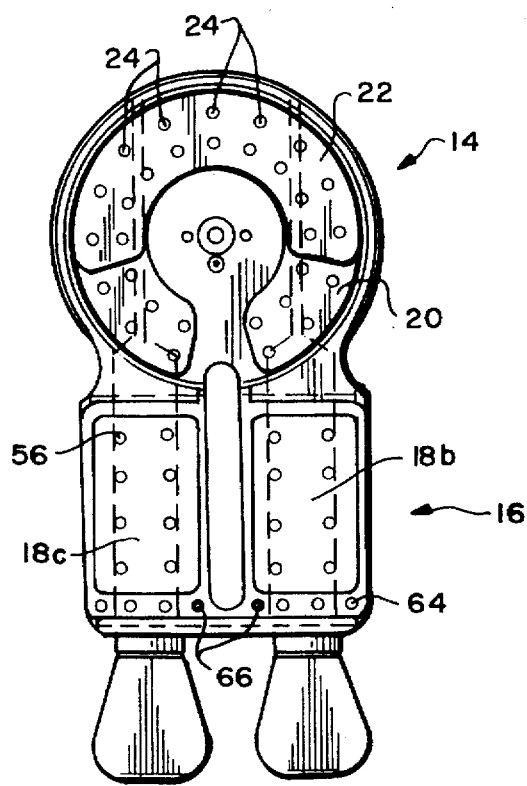
FIG. 3 is a top plan view, in partial cross-section, of the container of FIG. 1.

Referring to the drawings, and in particular, FIGS. 1–7, the sterilization and storage container of the present invention is indicated generally by numeral 10. The container consists of a base member 12, preferably formed of a high density polypropylene or the like. Base member 12 is generally palm or hand-sized, and includes a cylindrical portion 14 and a rectangular or square portion 16. One or more recesses or wells 18a, 18b, 18c are formed in body 12, for example, by casting or milling in known manner. As seen particularly in FIG. 3, well 18a includes a first shallow area 20 and a second deeper area 22, i.e. for accommodating different length instruments. A plurality of through holes 24 are drilled through body 12 running between the floor of well 18a, and the body bottom 26 for providing ingress and egress of sterilizing fluid and drainage of condensation.

A feature and advantage of the present invention is to provide a sterilization and storage container system particularly adapted for small instruments such as drill bits, pins, screws and the like, and which facilitates selection and removal of particular instruments.

Figure 5:
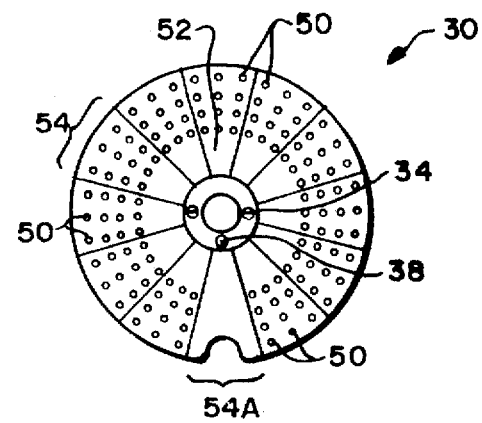
FIG. 5 is a top plan view showing details of the instrument support disk portion of the present invention.
Figure 6:
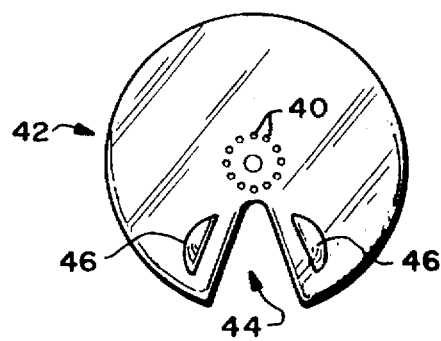
FIG. 6 is a top plan view showing details of the rotatable cover portion of the present invention.
Figure 4:
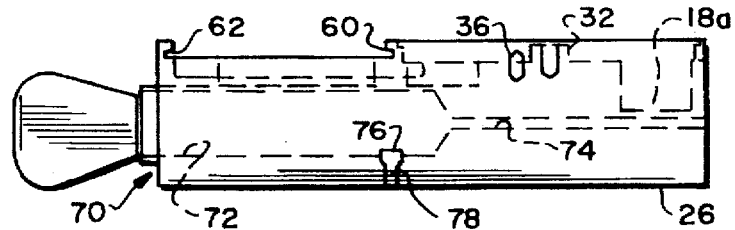
FIG. 4 is a side elevational view, in partial cross-section, of the container of FIG. 1.
Figure 7:
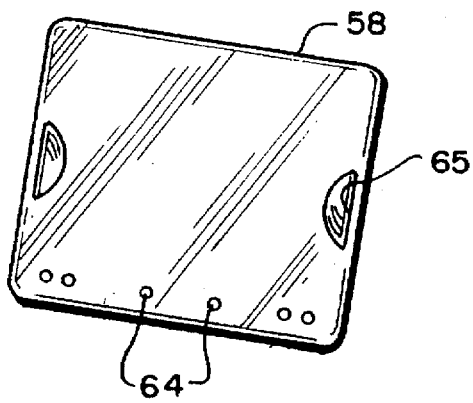
FIG. 7 is a top plan view of the slide cover portion of the present invention.

Referring also to FIGS. 5 and 6, an instrument support disk 30 is mounted on hub 32 formed centrally of base 12 cylindrical portion 14. Disk 30 is fixedly positioned on hub 32 by fastening means such as screws 34 which extend through holes (not shown) in disk 30 into hub 32. A detent ball 36 is positioned extending through an aperture 38 in disk 30 for cooperating with holes 40 in rotatably mounted cover 42 which overlies and is spaced from disk 30. As seen in particular in FIG. 6, cover 42 includes a cutout 44 for providing limited access to selected instruments held in disk 30 as will be described in detail hereinafter. Cover 42 also includes recesses 46 for engagement with the finger or thumb for rotating the cover. Preferably, cover 42 is spaced from disk 30 so as to permit ingress and egress of sterilization fluid at the top side of the disk.

Referring again to FIG. 5, disk 30 includes a plurality of apertures 50 which are sized to accommodate different diameter instruments such as drill bits, pins, screws or the like. In order to assist the surgeon in selecting the desired instrument, like instruments may be organized or grouped together in separate segments of the disk and identified by indicia printed on the top surface 52 of the disk. Cutout 44 in cover 42 is sized and shaped so as to expose only a single grouping or segment 54 at any one time. By way of example, disk 30 may be divided into twelve segments, 54 each comprising thirty degrees, while cutout 44 may comprise a segment or arc of approximately thirty-five degrees. One of the segments 54A is left undrilled, so as to provide a "parking" position for cover 42.

Wells 18b and 18c are formed in the rectangular portion 16 of body 12. As before, a plurality of through holes 56 run from the bottom of wells 18b, 18c to the bottom 26 of body 12 to provide for ingress and egress of sterilization fluid and drainage of condensation. A cover member 58 is slidably disposed over wells 18b, 18c and mounted in slots 60, 62 which are formed integrally with body 12. A plurality of holes 64 are formed along one edge of cover 58 for engaging with detents 66 which are mounted in body 12 adjacent slot 62. Cover 58 also includes a pair of recesses 65 for accommodating a fingernail or thumb nail in assisting in sliding cover 58 to expose instruments in wells 18b, 18c.

Covers 42 and 58 preferably are formed of a transparent polymeric material such as a polysulfone so that the instruments stored thereunder readily may be viewed by the surgeon. Completing the preferred embodiment of the invention, one or a pair of bores 70 are formed in an end of body 12 for accommodating and releasably storing an extraction tool for facilitating removal of instruments stored in the container. Bores 70 include a first large diameter section 72 for accommodating the handle portion of the extraction tool as will be described in detail hereinafter, and a small diameter section 74 for accommodating the tip and shank of the extraction tool. Finally, a strip 76 formed of a resiliently deformable material such as silicon rubber is mounted in a slot 78 which transverses in part large diameter section 72 of bores 70. Strip 76 releasably captures and holds the extraction tool for use by the surgeon.

Figure 8:
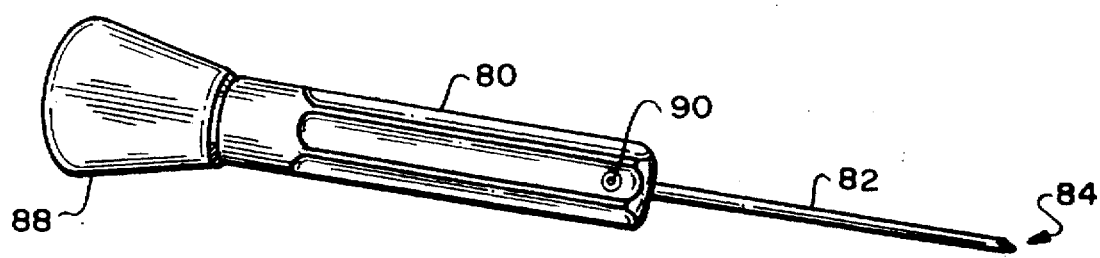
FIG. 8 is a side elevational view, and showing an extractor tool useful with a preferred embodiment of the present invention.
Figure 9:
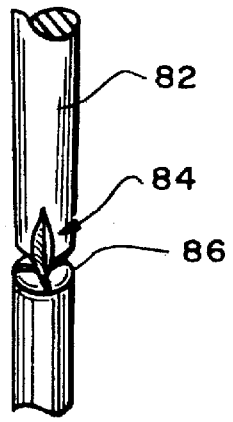
FIG. 9 is an enlarged view, and providing details of the distal end of the extractor tool of FIG. 8 shown engaging the top of a drill.

Referring now to FIGS. 8 and 9, the extraction tool useful in accordance with the present invention includes an elongate handle 80 through which is mounted an elongate shank 82 terminating at its distal end in a reverse cut wings 84 or the like for engaging the slotted ends 86 of an instrument such as a drill pin, screw or the like.

In a preferred embodiment, shank 82 extends completely through a bore in handle 80 and is fixedly positioned to a top piece 88. Shank 82 is rotatably mounted within handle 80 and is held in handle 80 by a screw detent 90 or the like which cooperates with an annular slot (not shown) on the shank 82.

It is thus seen that there has been provided in accordance with the present invention a sterilization and storage container particularly adapted for small surgical instruments such as drills, pins and screws. While particular embodiments of the present invention have been illustrated and described below, it is not intended to limit the invention, and changes and modifications may be made therein within the scope of the following inventions.

I claim:

1. A sterilization container for sterilizing, transporting, and storing surgical instruments, and comprising a base having a plurality of holes for permitting ingress and egress of sterilization fluid, said base having at least one bore for accommodating the handle portion of an extraction tool stored therein, said base further having at least one well, an apertured plate covering at least part of said well, said apertured plate having apertures to accommodate selected instruments, said apertured plate comprising a plurality of apertures grouped by size, and a cover rotatably mounted over and spaced from the apertured plate, said cover having an opening for providing access to a limited area of the plate and any instruments loaded therein.

2. In a sterilization container according to claim 1, and including indicia keyed to instruments, printed on a surface of the plate.

3. In a sterilization container according to claim 1, wherein said cover includes a plurality of holes for engagement by a detent extending above the plate.

4. In a sterilization container according to claim 1, wherein said rotatively mounted cover includes at least one recess for engagement with a finger or thumb for rotating the cover.

5. In a sterilization container according to claim 1, and comprising at least one additional well covered at least in part by a slidably mounted cover.

6. In a sterilization container according to claim 5, wherein said slidable cover includes at least one recess for engagement by a finger or thumb.

7. In a sterilization container according to claim 1, wherein said rotatable cover is spaced from the plate.

8. In a sterilization container according to claim 1, and further including means transversing said bore at least in part for releasably engaging the handle portion of an extraction tool stowed in said bore.

9. A sterilization container for sterilizing, transporting, and storing surgical instruments, and comprising a base having at least one well, an apertured plate covering at least part of said well, said apertured plate having apertures to accommodate selected instruments, a rotatable cover rotatably mounted over and spaced from the apertured plate, said cover having an opening for providing access to a limited area of the plate and any instruments loaded therein, said base including a plurality of through holes for permitting ingress and egress of sterilization fluid, said base further including at least one bore for accommodating an extraction tool stowed therein, and means transversing said bore at least in part for releasably engaging a tool stowed in said bore.

10. In a sterilization container according to claim 9, and including indicia keyed to instruments, printed on a surface of the plate.

11. In a sterilization container according to claim 9, wherein said cover includes a plurality of holes for engagement by a detent extending above the plate.

12. In a sterilization container according to claim 9, wherein said rotatively mounted cover includes at least one recess for engagement with a finger or thumb for rotating the cover.

13. In a sterilization container according to claim 9, and comprising at least one additional well covered at least in part by a slidably mounted cover.

14. In a sterilization container according to claim 13, wherein said slidable cover includes at least one recess for engagement by a finger or thumb.

15. In a sterilization container according to claim 9, wherein said means for engaging comprises a resiliently deformable strip transversing said bore at least in part.

* * * * *